United States Patent [19]

Anderson et al.

[11] Patent Number: 5,742,392
[45] Date of Patent: Apr. 21, 1998

[54] POLARIZED MATERIAL INSPECTION APPARATUS

[75] Inventors: Richard Rox Anderson, Lexington; William A. Farinelli, Danvers; Nikiforos Kollias, Watertown, all of Mass.

[73] Assignee: Seymour Light, Inc., Watertown, Mass.

[21] Appl. No.: 634,311

[22] Filed: Apr. 16, 1996

[51] Int. Cl.$^6$ ............................................. G01N 21/21
[52] U.S. Cl. .................................... 356/364; 356/369
[58] Field of Search .................................. 356/364, 366, 356/367, 369; 250/225

[56] References Cited

U.S. PATENT DOCUMENTS

| | | |
|---|---|---|
| 2,120,365 | 6/1938 | Kriebel. |
| 2,866,375 | 12/1958 | Wells et al.. |
| 2,947,212 | 8/1960 | Woods. |
| 3,062,087 | 11/1962 | Zandman et al.. |
| 3,633,212 | 1/1972 | Cooper. |
| 3,847,481 | 11/1974 | Paraskevas et al.. |
| 3,904,293 | 9/1975 | Gee. |
| 4,007,979 | 2/1977 | Coblitz. |
| 4,398,541 | 8/1983 | Pugliese. |
| 4,482,250 | 11/1984 | Hirvonen et al.. |
| 4,846,184 | 7/1989 | Comment et al.. |
| 4,957,368 | 9/1990 | Smith ............................. 356/369 |
| 5,053,704 | 10/1991 | Fitzpatrick. |
| 5,198,875 | 3/1993 | Bazin et al.. |
| 5,343,536 | 8/1994 | Groh. |
| 5,370,114 | 12/1994 | Wong et al.. |
| 5,426,506 | 6/1995 | Ellingson et al. ............... 356/369 |
| 5,442,489 | 8/1995 | Yamamoto et al.. |
| 5,452,716 | 9/1995 | Clift. |

FOREIGN PATENT DOCUMENTS

WO92/12404   7/1992   WIPO ............................ 356/369

OTHER PUBLICATIONS

Hart, IBM Technical Disclosure Bulletin, vol. 1, No. 5, Feb. 1959, pp. 18 and 19.
Prutton et al, Journal of Scientific Instruments, vol. 40, No. 10, Oct. 1963, pp. 490–493.
Van Doorne, J. Chem. Educ., vol. 47, No. 10, Oct. 1970, p. 699.

*Primary Examiner*—F. L. Evans
*Attorney, Agent, or Firm*—Devine, Millimet & Branch, P.A.

[57] ABSTRACT

Light reflected from skin has two components: regular reflectance, or "glare" arising from the surface, and light backscattered from within the tissue. The regular reflectance contains the visual cues related to surface texture, whereas the backscattered component contains the cues related to pigmentation, erythema, infiltrates, vessels and other intracutaneous structures. Unlike the backscattered component, regular reflectance preserves the plane of polarization of polarized incident light. Thus, viewing skin through a linear polarizer, under linearly polarized illumination, separates the two components of tissue reflectance. When the planes of polarization are parallel, images with enhanced surface detail are obtained. When the planes are orthogonal, wrinkles and surface detail disappear, and an enhanced view of vasculature and pigmented lesions is obtained. Apparatus for performing such inspection is disclosed.

7 Claims, 3 Drawing Sheets

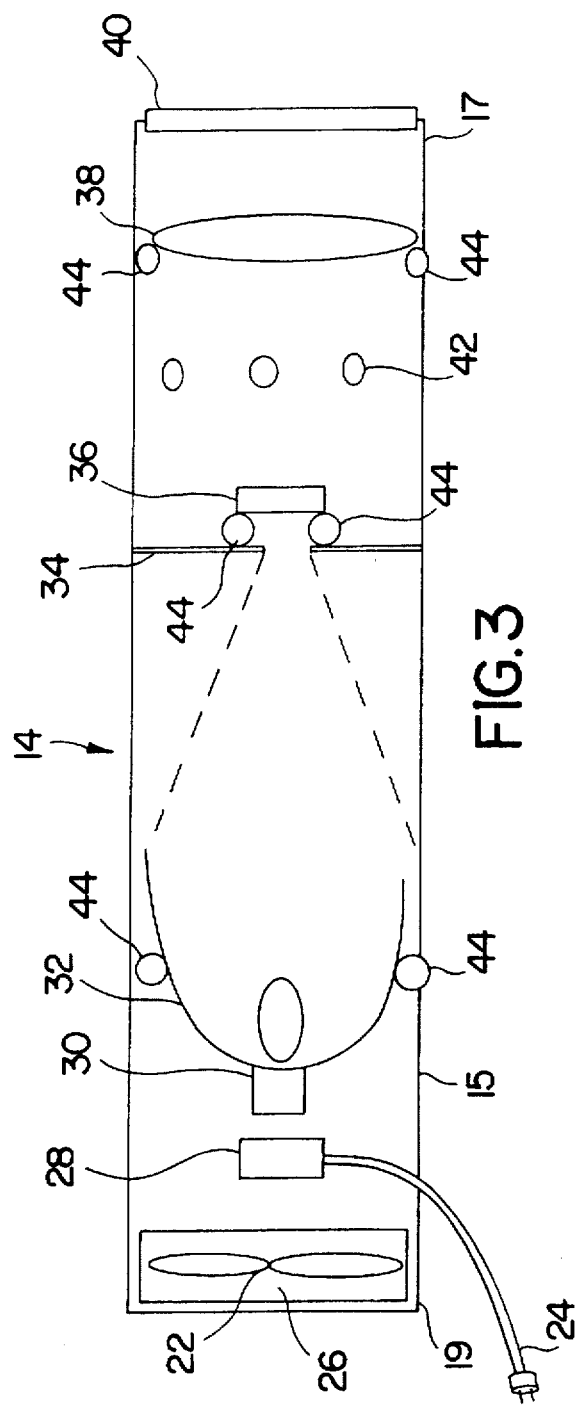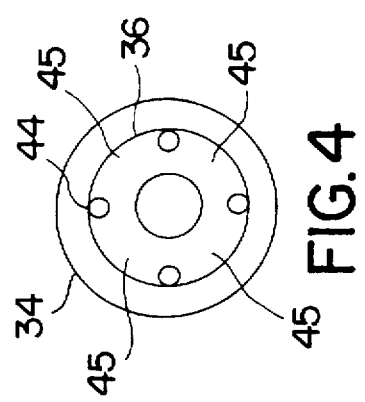

5,742,392

POLARIZED MATERIAL INSPECTION APPARATUS

FIELD OF THE INVENTION

The present invention relates to a device for evaluating the surface and sub-surface properties of skin, particularly by irradiating the surface of the skin with adjustable polarized light and viewing the optical reflectance through a polarizing viewer.

BACKGROUND OF THE INVENTION

The prior art discloses a number of devices utilizing polarized light for surface irradiation and reflectance inspection. For example, U.S. Pat. No. 2,120,365 to Kriebel discloses the use of polarizing lenses in eye-glasses for orthogonally polarizing light being viewed. The light originates from a source located on the side of an object or material of interest opposite to the viewer which allows for examining the photo-elastic effects of the light bending around the object.

Another reference, U.S. Pat. No. 2,947,212 to Woods shows detection of surface conditions of sheet metal by irradiating a surface with polarized light and using a polarizer in the optical path of the detector. This allows for only the viewing the intensity of the polarized light while eliminating all extraneous light rays. Similarly, U.S. Pat. No. 3,904,293 to Gee uses linearly polarized light to irradiate a surface and then detection of the reflected light. Prior to the reflected light being detected, it must first pass through a polarizing beam splitter which separates the light into its principal polarized (incident) and orthogonally polarized (depolarized) wave components. These two distinct waves are then detected by different detectors and changes in the surface texture will cause corresponding changes in the detected signal characteristics to be compared.

U.S. Pat. No. 5,053,704 to Fitzpatrick is for imaging a surface to detect cracks, flaws, voids, and the like. To do this, a magneto-optical substrate including a conductive sheet is laid over the target material. A current is passed through the conductive sheet to provide a biased magnetic field. Polarized light is then directed through the substrate into the target material and the reflected light is viewed through a separate linear polarizer. The biased magnetic field induces a rotation of the plane of polarization of the incident projected light such that viewing the reflection through a linear polarizer will render flaws visible.

Further, U.S. Pat. No. 5,198,875 to Bazin et al also teaches irradiation of a surface with polarized light. Bazin et al sets up two detectors, one at an angle of reflectance equal to the angle of incident while another detector is located perpendicularly to the surface. The reflected polarized light is passed through polarization separation cubes and eventually four detectors detect the reflected light. These detectors are connected through an electronic processing means which evaluates the various signals for brightness comparison.

Another prior art reference is U.S. Pat. No. 5,442,489 to Yamamoto et al relates to a magnifying apparatus. A polarized light irradiates an object and the reflected light is transmitted through a polarizing means and is in turn imaged by an imaging device. This arrangement magnifies and images practical areas of interest.

Applicant's article, "Polarized Light Examination and Photography of the Skin" by Rox Anderson, MD, which appeared in the Archives of Dermatology, July 1991, volume 127, pages 1000–1005, describes the failings in the art to provide adequate viewing of surface and subsurface epidermis and is shown in FIG. 1. Light reflected from skin has two components: regular reflectance, or "glare" arising from the surface, and light backscattered from within the tissue. The regular reflectance contains the visual cues related to surface texture, whereas the backscattered component contains the cues related to pigmentation, erythema, infiltrates, vessels and other intracutaneous structures. Unlike the backscattered component, regular reflectance preserves the plane of polarization of polarized incident light. Thus, viewing skin through a linear polarizer, under linearly polarized illumination, separates the two components of tissue reflectance. When the planes of polarization are parallel, images with enhanced surface detail are obtained. When the planes are orthogonal, wrinkles and surface detail disappear, and an enhanced view of vasculature and pigmented lesions is obtained. The prior art discloses various devices and methods that accomplish surface irradiation and reflection detection. However, none of the prior art devices or methods provide a means or method of illuminating a surface and then view either surface or subsurface reflectance at the discretion of the user. Furthermore, the prior art does not disclose, teach or even suggest the preferred embodiment claimed.

The prior art also requires elaborate and often fixed setups to perform any type of surface analysis. These setups usually require the surface of interest to be moved past a positioned optical array. There is little teaching of portable units which would enable the imaging to be done in remote locations or manipulate the illuminator source with respect to the object being viewed.

Another problem in the art is cost. To set up these systems takes funds to procure the equipment needed. The art fails to account for users that need a practical system but have limited resources.

Another problem is space. These systems are usually quite large and need the area to set them up and leave them in place.

SUMMARY OF THE INVENTION

It is an object of this present invention to provide a device for irradiating a surface with polarized light in association with a polarized viewing means that provides separation between surface and subsurface reflection.

It is another object to provide that the light source and viewing means are to be integrally connected.

It is another object to provide that the light source and viewing means are of such a size and weight as to be comfortably wearable by a user.

It is another object to provide that either the surface or subsurface reflectance can be viewed alternatively and at the discretion of the user.

The foregoing objects are met using a device for object or material inspection comprising an illuminator and a support means. The illuminator itself comprises a housing having a first and second end located at opposite ends thereof. The housing encloses the optical components and forms an optical path. The components within the housing include a light source located at one end thereof, a first polarizing means connected to the housing and located in the optical path between the light source and the object or material to be inspected. The housing also includes a lens located in said optical path between the light source and the object or material, an aperture located in the optical path intermediate the light source and the lens, and an optical filter located in the optical path between the light source and the object or material.

The support means includes a means for attaching the illuminator housing to the supporting means in a preferred orientation and a viewing means. The viewing means comprises a second polarizing means through which a object or material is inspected.

DESCRIPTION OF THE DRAWINGS

FIG. 3 is a diagrammatic view showing the relationship of the internal elements of the irradiating source of the housing of FIG. 2.

FIG. 4 is a plane view depicting the aperture of the irradiating source of FIG. 3.

DETAILED DESCRIPTION

Figure 1:
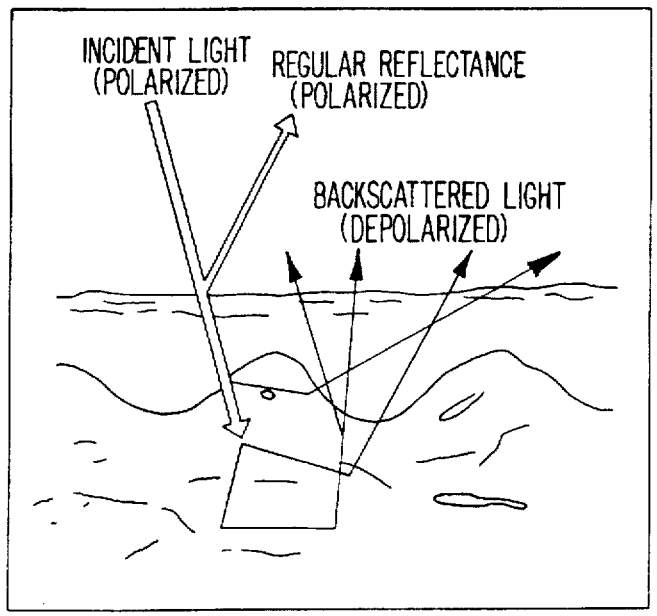
FIG. 1 is a plain view of a schematic representation of the two components of skin reflectance as discussed in the prior art.

Referring to FIGS. 2 through 6, a device 10 for object or material analysis includes a support means 12 and a illuminator 14. The illuminator 14 is fixedly attached to the support means 12 in a preferred orientation. This arrangement allows for the illuminator 14 to be aligned in unison with the position of the support means 12 so as to eliminate adjustment variables during operation of the device. The support means 12 comprises a support adjustable means 16 for maintaining the preferred orientation of the support means 12. One skilled in the art would recognize that the use of a strap, VELCRO® hook and loop fasteners or other types of fasteners could be used as the support adjustable means 16.

Further, a bridge means 18 for supporting the illuminator 14 is fixedly attached to the support means 16. Many types of well known object or materials including plastics, cloths or composites can be used to form the bridge means 18. Also, the bridge means 18 aids in maintaining the preferred orientation of the support 12 while in use. Filters 20 and 22 are polarizing elements that may be located on the support 12 and are proximate each other. Further, filters 20 and 22 are maintained in a preferred orientation with respect to the illuminator 14. The orientation is such that each of the illuminator 14 and filters 20 and 22 will face an object or material of interest simultaneously. Each filter is combined with a magnifying lens 20' and 22' selected to provide a magnified view of the surface being inspected which coincides with the illuminated area. However, it should be recognized that the dual filter and lens construction shown by filters 20 and 22 and lenses 20' and 22' can be replaced by a single filter/lens design. Also, separate filters and or lenses can be used in conjunction with the device in place of an integral filter and lens arrangement.

Figure 2:
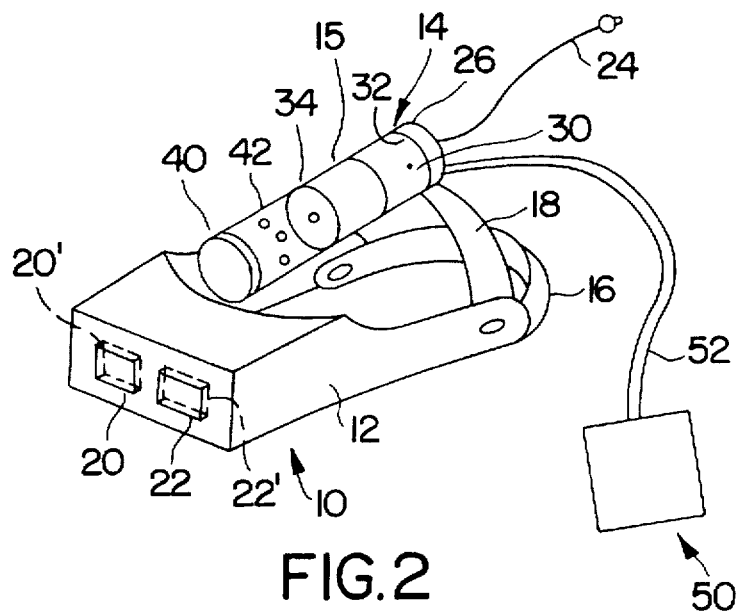
FIG. 2 is a perspective view of the present invention.
Figure 5:
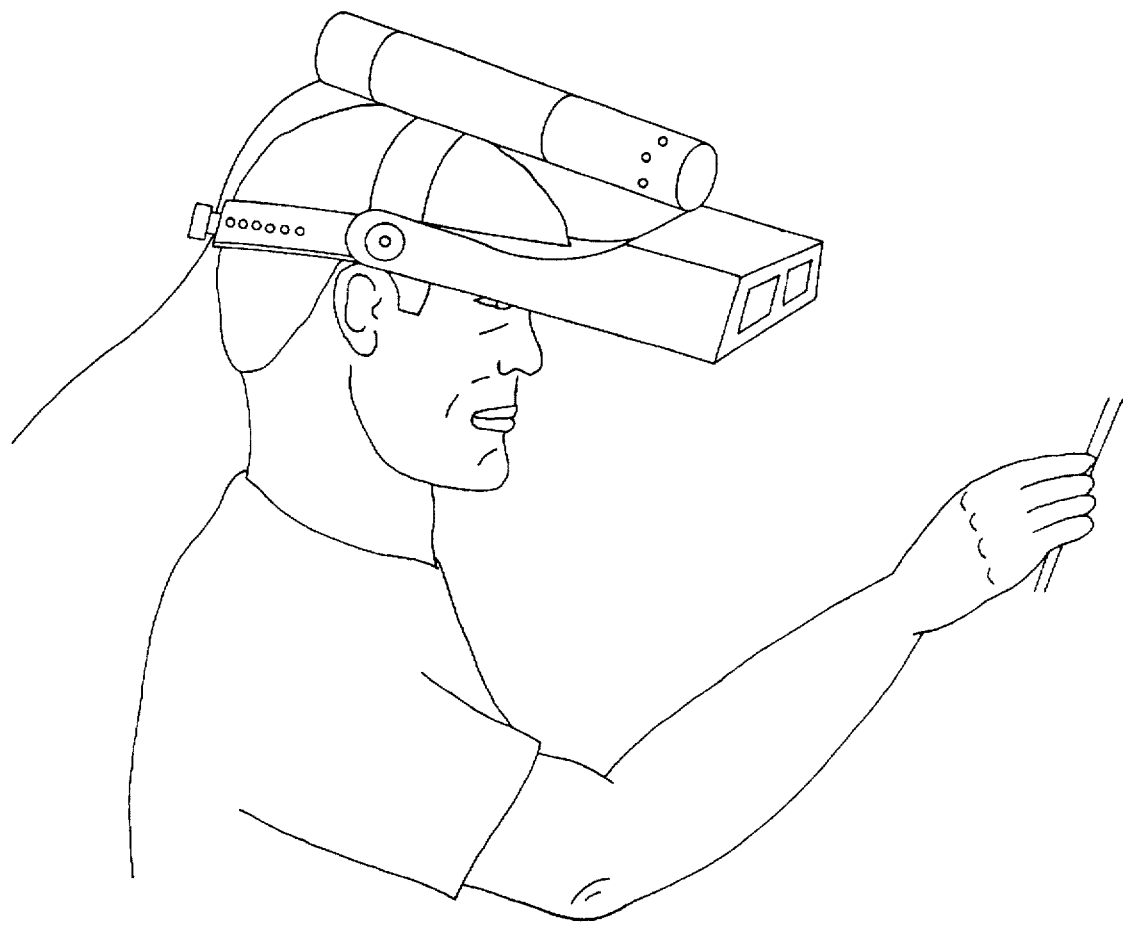
FIG. 5 is a perspective view of an individual using the present invention of FIG. 2.

The embodiment shown in FIGS. 2 and 5 includes a support means configured to be worn on the head of a user, such as a physician in an operating room or like environment. It should be appreciated that other embodiments can be envisioned that fall within the spirit and scope of the invention, such as internal medicine examination devices, which use fiber-optic means for both illuminating and viewing internal organs or the like. The invention can be used for enhancing the examination of any object in which specular and diffuse reflectances are desired to be viewed separately.

The illuminator 14 incorporates a plurality of elements, which in concert, provide substantially uniform polarized light to irradiate a site of interest. The illuminator 14 includes a housing 15 having a first end 17 and a second end 19, which forms an optical path and houses the illuminator elements. The preferred orientation is positioning the first end 17 so that it is closer to the filters 20 and 22 than the second end 19. A power supply means 24 connects to the internal components of the housing 15 to supply power to the system's components requiring the same.

The elements of the illuminator 14 are better seen in FIG. 3, which is a diagrammatic representation of the relationship of the internal elements of the device. First, a light source 30 is used to provide light to illuminate the object or material to be inspected. Lamps can be obtained in various sizes and luminosities. The light source 30 is located inside a reflector 32, preferably at its focus. The reflector 32 is an elliptical shape, opening out such that the light reflected from the elliptical shape is directed down the optical path formed by the structure of the housing 15. The reflected light is focused by reflector 22 at an aperture 34. The focused light passes through aperture 34 and an infrared blocking, visible light passing filter 36. The location of these optical elements is not critical, however, the aperture is chosen to pass a uniform field efficiently, and care should be taken in maximizing the amount of light incident on the object or material of interest. There are a number of various elements that can be chosen as the light source 30. Some of these include, but are not limited to, incandescent lamps, tungsten-halogen lamps, various bulbs and filament arrangements. The use of polarizers (see below) limits the total visible light to only about 1/10 of that occurring without the polarizers. Therefore, a bright light source is needed. However, a typical light source 30 having the required intensity generates a vast amount of heat, typically 20–40 watts. Since the light source 30 generates is confined inside the housing 15, the heat needs a way to be dissipated. Therefore, in order to dissipate the heat generated by the light source 30, a cooling means 26 is located within the housing 15 at the second end 19 thereof.

Figure 6:
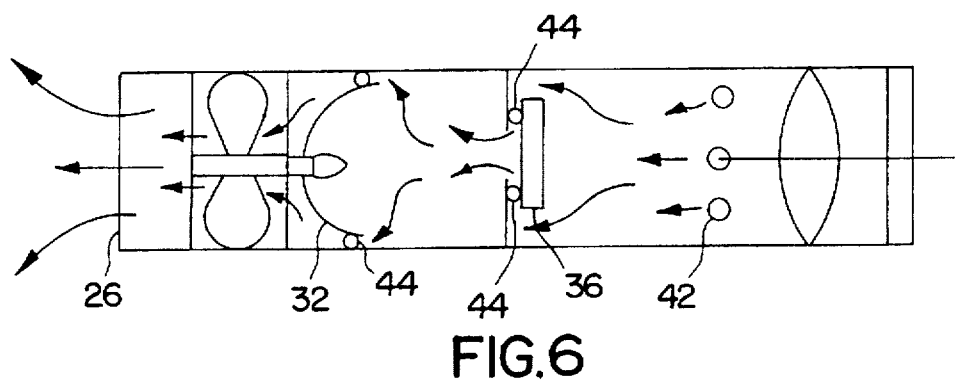
FIG. 6 is a diagrammatic view showing the convection cooling flowpath through the housing.

In the embodiment shown in the figures, the cooling means 26, which is used to dissipate the heat generated by the light source 30, is a convection cooling means, which includes an exhaust fan 27. The exhaust fan 27 provides sufficient convective cooling to the illuminator components located within the housing by drawing cooler air from outside the illuminator 14 into the interior of housing 15. The air is drawn into and then out of the device via the exhaust fan 26 as illustrated in FIG. 6. There are openings 42 in the housing 15 that allow air to flow into the system. These openings 42 could be constructed in many well known fashions including holes, slits and perforations with or without screens or filters covering the openings. The minimum size requirement of the openings must be enough to allow a sufficient amount of air to enter and cool the system. The cooling means 26 is incorporated into the system to extend the device's 10 useful life. Further, by maintaining the device 10 at a moderate temperature, a user can handle the device 10 safely and without the need for special protection from burn injuries such as protective gloves, or the like.

The power adapting means 28 can be a switching device, AC/DC converter, battery, or the like. Further, it should be recognized that the power adapting means 28 is also electrically connected (not shown) to the light source 30.

The infrared filter 36 is used to attenuate infrared light that is generated by the light source 30. If too much infrared light is directed at the object or material of interest for a prolonged period of time, unwanted heating and/or damage can occur to the surface. For instance, if as disclosed the object were human skin, prolonged exposure to infrared light might prove uncomfortable or harmful, for example by altering blood perfusion, which could result in an erythematous reaction.

As indicated above, elliptical reflector 32 is selected to focus a beam of light at aperture 34 such that the light passing through aperture 34 is substantially uniform throughout the cross-section of aperture 34. Lens 38 is then used to project a real image of aperture 34 onto the object to be inspected resulting in a substantially uniform, bright spot of illumination. The spacing between lens 38 and aperture 34 is selected to produce a conjugate ratio to project a magnified image of the aperture onto an object, for example, skin, at a working distance. The working distance is substantially a distance from lens 38 equal to the focal plane of magnifying lenses 20' and 22'. In one embodiment of the invention, the lens is a fixed focal length lens and is not adjustable. This eliminates operational variables during use of the device.

A first polarizing means 40 is located at an end of the housing. The polarizing means 40 is a linearly polarizing lens that polarizes the light from the light source 30 in a single plane of polarization. This allows for polarized light to irradiate the object or material of interest as shown in FIG. 5. The polarizing lens 40 is rotatable to any position in between a first position and a second position. By rotating the polarizing lens 40, different planes of polarization can be achieved.

The reflector 32, infrared filter 36 and lens 38 are all spatially maintained in the system via a plurality of attachment means 44. The plurality of attachment means 44 maintain each of the respective elements in the optical path but with minimal contact with the housing 15 to limit conductive heating of the housing, and to allow for the air flowing within the housing to circumvent and cool the elements. Further, this provides for a more efficient cooling of the air in the system and cooling of the individual elements.

The attachment means 44 are adhesive spacers that maintain the elements in a desired orientation and relative position while allowing gaps 45 for flowing air to pass by. FIG. 4 shows the adhesive spacers being constructed by placing a predetermined amount of an adhesive in intervals along a surface such as the housing or aperture. Then, by overlaying the adhesive with an element and adhering the element to the surface, a space is formed at the same time the element becomes rigidly attached. In FIG. 4, the infrared filter 36 would be attached to the aperture 34 via adhesive spacers 44.

Though adhesive spacers 44 have been disclosed as the attachment means, other types of attachment and spacing means could be used. This includes welding, soldering and other mechanical joining means being use to adhere the elements to their respective surfaces, and clamps which grasp the elements of the housing while allowing air to flow therethrough.

In FIG. 5, the linearly polarized light impinges on the surface of the material or object under examination at an angle. When incident and detected planes are parallel, the regular (Fresnel) reflectance component is attenuated less than the depolarized backscattered component. This causes relative enhancement of the regular reflectance component. When the incident and detected planes of polarization are perpendicular (crossed), the regular reflectance is entirely eliminated from detection.

In the claimed invention, a first and second polarizing means are used in concert with each other. Further, this allows for the detection of reflected light to be from the backscattered light. Illuminator 14 irradiates the surface with linearly polarized light generated by light passing through the first polarizer 40 oriented in a first position. The backscattered light is detected by a user via a second set of fixed polarized filters 20 and 22 and magnifying lenses 20' and 22'. In the first position, the plane of polarization of the first polarizer 40 is parallel to the plane of polarization of filters 20 and 22. Thus, the light reflected from the surface allows the user to view surface properties. By rotating either the first polarizer 40 or the polarized filters 20 and 22 to a second position 90° from the first, perpendicular axes of polarization are formed between the first polarizer 40 and the polarized filters 20 and 22. This allows the user to view subsurface features of the skin, tissue or other material to be inspected.

The change between the incident and detected planes from parallel to perpendicular is caused by the rotation of the polarizer 40 from one position to another and preferably from a first, predetermined position to a second, predetermined position. The total amount of rotation between the first and second predetermined positions is 90°. The user can also choose to vary the amount of rejection of surface reflectance by selecting adjusting the polarizers intermediate their first and second predetermined positions.

The cooling flow path is seen in FIG. 6. Air, from outside the system, is drawn into the system through openings 42 by the exhaust fan 26. The air follows the path of the arrows. It flows around the edges of the infrared filter 36 and the reflector 32 through spaces created by the adhesive spacers 44 which hold the filter 36 and reflector 32 in their respective positions within housing 15 thus cooling all the elements. It then continues out of the system past the exhaust fan 26.

Although the cooling device has been disclosed as an exhaust fan, other types of cooling devices such as thermoelectric cooling systems can be employed. A liquid fluorocarbon refrigerant system, such as a miniaturized refrigeration system, or the like, can be used to maintain a constant temperature in the system. Further, a liquid cooling system 50 could be used wherein water in a circulating path is used to remove heat. Here, a means such as a tube 52 can be used to circulate cool water through the device. Heat from the system is then transferred to the cool water which is in continuous circulation. The water is then cooled and recirculated back through the system.

Although the polarizing filter 40 has been disclosed at the end of the housing, it should be recognized that the polarizing filter can also be incorporated within the housing or as a coating on one of the other optical elements. Further, to rotate the polarizing filter from the first position to the second position, the polarized lens could be attached to an external lever that is used to rotate it within the housing. This allows for the placement of the polarizing filter to be in various regions of the housing so long as it is located within the optical path formed between the light source and the object or material being irradiated.

As with the polarizing filter, the infrared filter can be placed in various regions within the housing so long as it is located within the optical path formed between the light source and the object or material being irradiated.

Although the present invention has been described with preferred embodiments, workers skilled in the art will recognize that changes may be made in form and detail without departing from the spirit and scope of the invention.

What is claimed:

1. An apparatus for material inspection comprising: an illuminator, said illuminator comprising a housing, said housing forming an optical path and housing a plurality of illuminator elements, said illuminator elements comprising a light source, a first polarizing means having a first plane of polarization, a lens, an aperture, an optical filter; a means for supporting said illuminator in a preferred orientation; and a viewing means, said viewing means comprising a second polarizing means having a second plane of polarization, wherein said first and second polarizing means are rotationally positionable with respect to each other such that their respective planes of polarization may be aligned in either a parallel or orthogonal relationship and wherein said means for supporting said housing comprises a headgear system, which allows said illuminator to be worn on the head of a user of the apparatus.

2. The apparatus for material inspection of claim 1, further comprising a cooling means for removing heat generated by said light source.

3. The apparatus for material inspection of claim 1, wherein said optical filter is an infrared-attenuating, visible-transmitting filter.

4. The apparatus for material inspection of claim 2, wherein said cooling means comprises a convection flow-path through said housing.

5. The apparatus for material inspection of claim 4 wherein said cooling means further comprises a fan for forced convection heat removal.

6. The apparatus for material inspection of claim 2, wherein said cooling means comprises a liquid cooling system.

7. The apparatus for material inspection of claim 1, wherein said second polarizing means is integral with said supporting means.

* * * * *